United States Patent
Den Boef

(10) Patent No.: US 9,952,518 B2
(45) Date of Patent: Apr. 24, 2018

(54) INSPECTION METHOD AND APPARATUS AND LITHOGRAPHIC APPARATUS

(71) Applicant: ASML Netherlands B.V., Veldhoven (NL)

(72) Inventor: Arie Jeffrey Den Boef, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/105,339

(22) PCT Filed: Nov. 14, 2014

(86) PCT No.: PCT/EP2014/074661
§ 371 (c)(1),
(2) Date: Jun. 16, 2016

(87) PCT Pub. No.: WO2015/090773
PCT Pub. Date: Jun. 25, 2015

(65) Prior Publication Data
US 2016/0320712 A1    Nov. 3, 2016

(30) Foreign Application Priority Data
Dec. 19, 2013   (EP) .................................... 13198288

(51) Int. Cl.
*G03F 7/20* (2006.01)
*G01N 21/956* (2006.01)
(Continued)

(52) U.S. Cl.
CPC ..... *G03F 7/70625* (2013.01); *G01N 21/4788* (2013.01); *G01N 21/956* (2013.01);
(Continued)

(58) Field of Classification Search
CPC .. G03F 7/70625; G03F 7/70633; G03F 7/705; G03F 7/70616; G01B 2210/56;
(Continued)

(56) References Cited

U.S. PATENT DOCUMENTS

| 4,933,567 A | 6/1990 | Silva et al. |
| 7,916,284 B2 | 3/2011 | Dusa et al. |

(Continued)

FOREIGN PATENT DOCUMENTS

| CN | 101109910 A | 1/2008 |
| CN | 101510051 A | 8/2009 |

(Continued)

OTHER PUBLICATIONS

Yoo et al. "Design of Multi-Wavelength Micro Raman Spectroscopy System and its Semiconductor Stress Depth Profiling Applications," Applied Physics Express 2 116502, The Japan Society of Applied Physics, Nov. 6, 2009; pp. 1-3.

(Continued)

*Primary Examiner* — Steven H Whitesell Gordon
(74) *Attorney, Agent, or Firm* — Sterne, Kessler, Goldstein & Fox P.L.L.C.

(57) ABSTRACT

Disclosed are an inspection method and apparatus and an associated lithographic apparatus. The inspection method comprises illuminating a structure with inspection radiation of a selected wavelength, the structure being of a type comprising a plurality of layers (for example a 3D memory structure). The resultant diffraction signal is detected a physical property of a subset of said layers is determined from said diffraction signal. The subset of layers for which said physical property is determined is dependent upon the selected wavelength of the inspection radiation.

20 Claims, 6 Drawing Sheets

(51) Int. Cl.
*G01N 21/47* (2006.01)
*G01N 21/88* (2006.01)

(52) U.S. Cl.
CPC ...... *G03F 7/70616* (2013.01); *G01B 2210/56* (2013.01); *G01N 2021/8845* (2013.01)

(58) Field of Classification Search
CPC .................. H01L 22/12; G01N 21/956; G01N 2021/8845; G01N 21/4788
See application file for complete search history.

(56) References Cited

U.S. PATENT DOCUMENTS

| | | |
|---|---|---|
| 2007/0081151 A1 | 4/2007 | Shortt et al. |
| 2010/0007872 A1 | 1/2010 | Isozaki et al. |
| 2012/0122252 A1 | 5/2012 | Fujimori |
| 2012/0123748 A1* | 5/2012 | Aben .................. G03F 7/70483 703/2 |
| 2013/0035888 A1* | 2/2013 | Kandel ............... G03F 7/70633 702/81 |
| 2013/0304424 A1 | 11/2013 | Bakeman et al. |
| 2014/0019097 A1 | 1/2014 | Bakeman et al. |

FOREIGN PATENT DOCUMENTS

| | | |
|---|---|---|
| JP | 2008-218799 A | 9/2008 |
| JP | 2009-511878 A | 3/2009 |
| JP | 2013-534044 A | 8/2013 |
| JP | 2015-531056 A | 10/2015 |
| WO | WO 2012/063859 A1 | 5/2012 |

OTHER PUBLICATIONS

International Search Report and Written Opinion of the International Search Authority directed to related International Patent Application No. PCT/EP2014/074661, dated Apr. 21, 2015; 9 pages.

International Preliminary Report on Patentability directed to related International Patent Application No. PCT/EP2014/074661, dated Jun. 21, 2016; 6 pages.

* cited by examiner

INSPECTION METHOD AND APPARATUS AND LITHOGRAPHIC APPARATUS

CROSS-REFERENCE TO RELATED APPLICATIONS

This application claims the benefit of EP application 13198288, which was filed on Dec. 19, 2013 and which is incorporated herein in its entirety by reference.

FIELD

The present invention relates to methods of inspection usable, for example, in the manufacture of devices by lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Three dimensional or vertical architectures, such as 3D NAND flash memory layer stacks, present challenges in accurate control, and therefore accurate measurement, of physical properties of the layer stacks. Such physical properties may comprise layer thickness or critical dimension of holes formed in the layer stack structure.

SUMMARY

It is desirable to provide a method and system enabling more accurate measurement of physical properties of structures such as layer stacks.

According to an aspect of the invention, there is provided an inspection method comprising: illuminating a structure with inspection radiation of a selected wavelength, wherein said structure comprises a plurality of layers; detecting a diffraction signal arising from said illumination of said structure; and determining a physical property of a subset of said layers from said diffraction signal, the subset of layers for which said physical property is determined being dependent upon the selected wavelength of the inspection radiation.

According to a second aspect of the present invention, there is provided an inspection apparatus comprising: a radiation source operable to illuminate a structure with inspection radiation of a selected wavelength, wherein said structure comprises a plurality of layers; a detector for detecting a diffraction signal arising from said illumination of said structure; and a processor operable to determine a physical property of a subset of said layers from said diffraction signal, the subset of layers for which said physical property is determined being dependent upon the selected wavelength of the inspection radiation.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
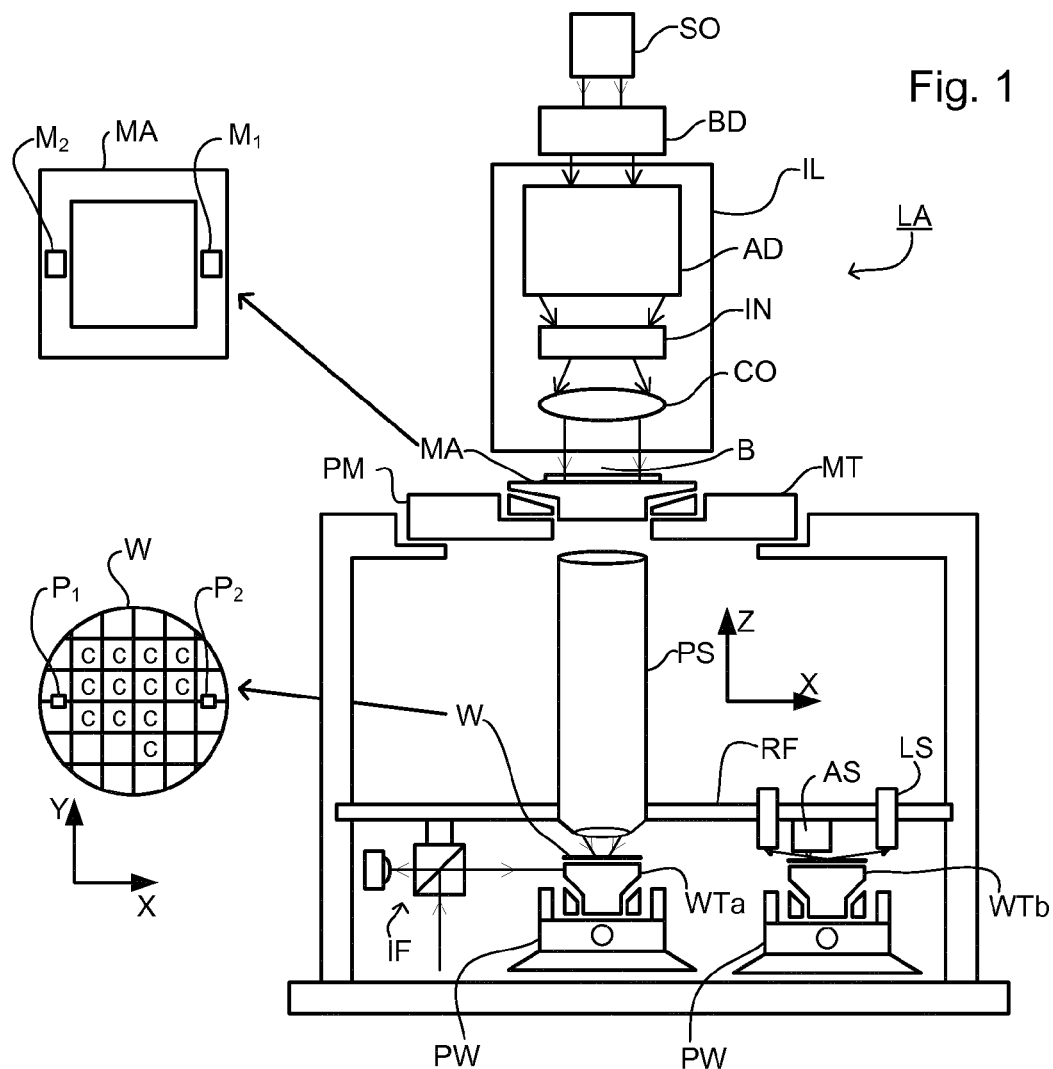
FIG. 1 depicts a lithographic apparatus.

FIG. 1 schematically depicts a lithographic apparatus. The apparatus comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g.

a resist-coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable minor array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing minors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as $\sigma$-outer and $\sigma$-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
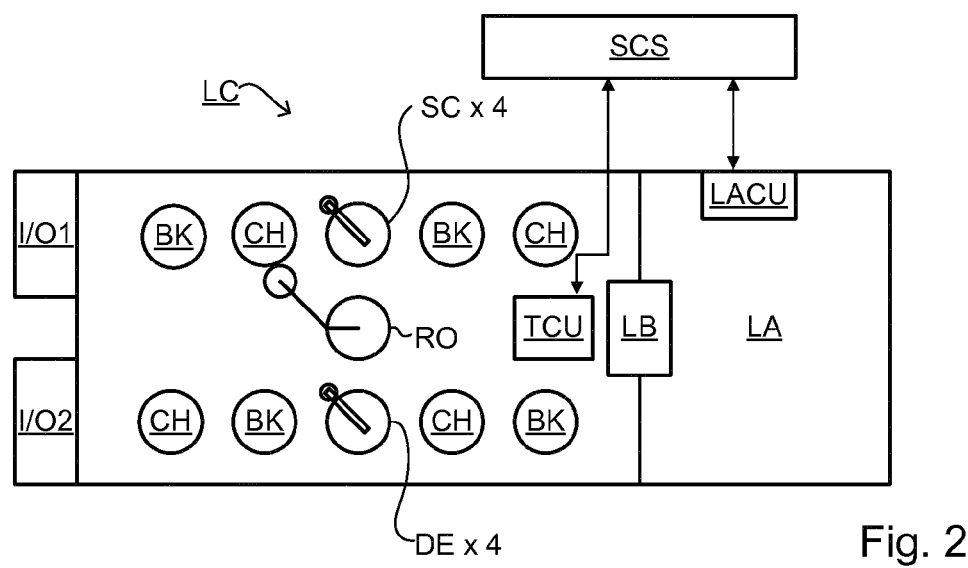
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked to improve yield or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast there is only a very small difference in refractive index between the parts of the resist which have been exposed to radiation and those which have not and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
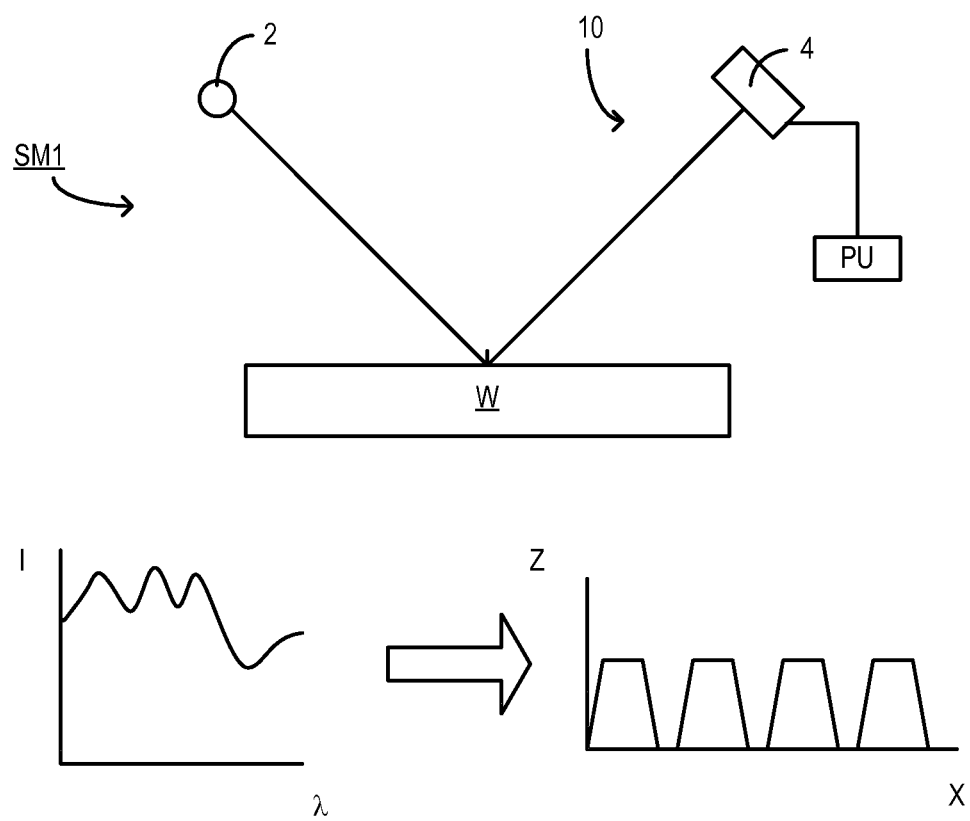
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
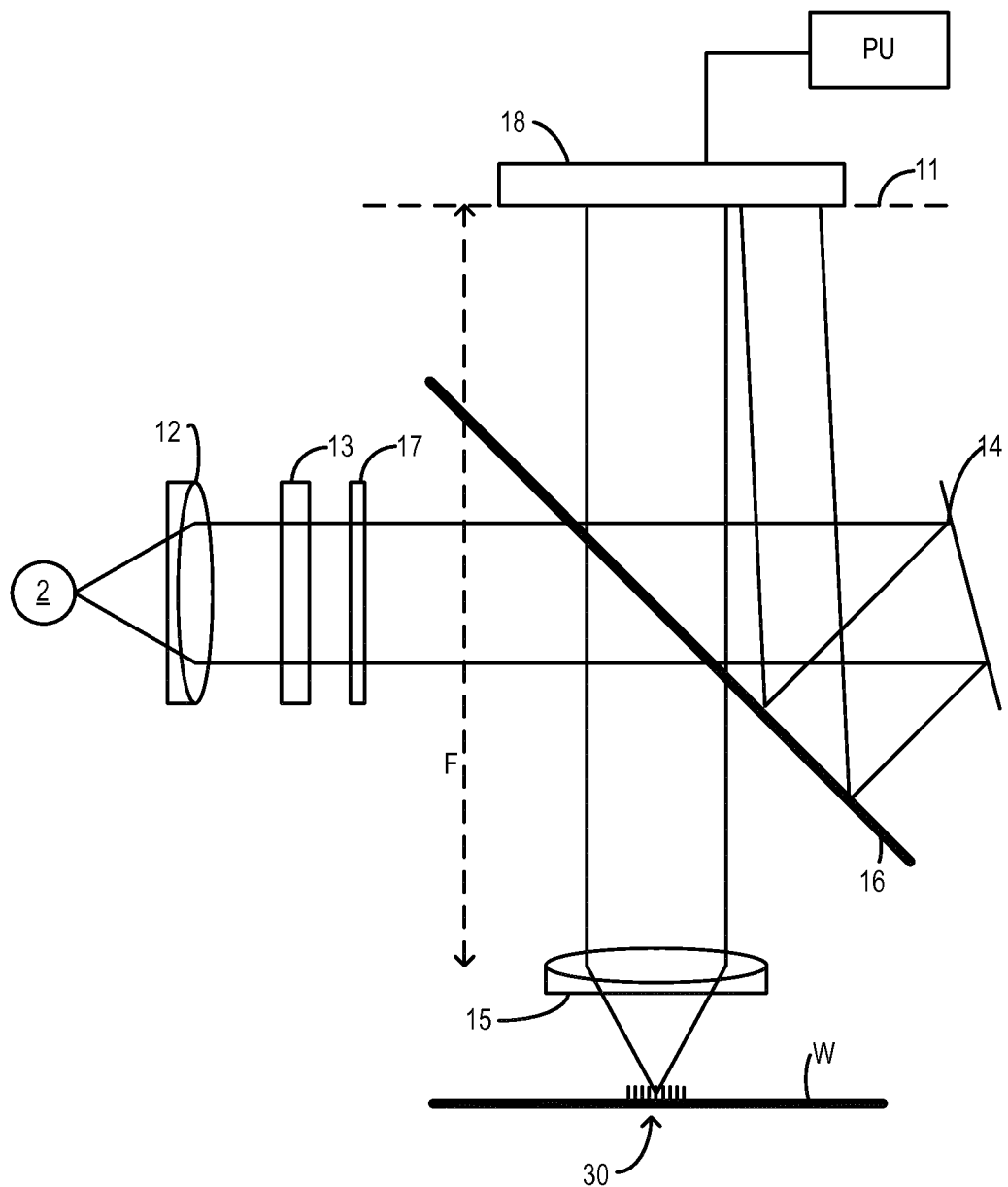
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
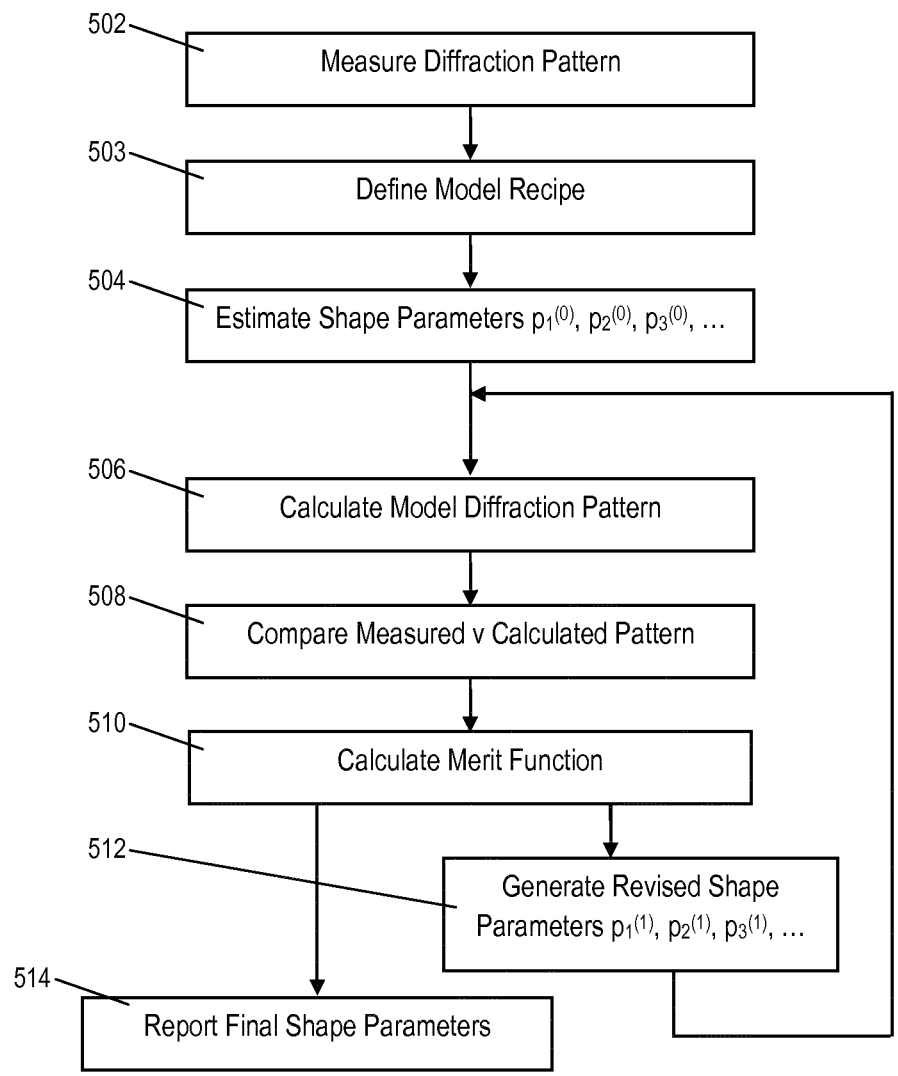
FIG. 5 depicts a first example process for reconstruction of a structure from scatterometer measurements.

Referring to FIG. 5 in more detail, the way the measurement of the target shape and/or material properties is carried out will be described in summary. The target will be assumed for this description to be periodic in only 1 direction (1-D structure). In practice it may be periodic in 2 or 3 directions (2- or 3-dimensional structure), and the processing will be adapted accordingly.

502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

503: A 'model recipe' is established which defines a parameterized model of the target structure in terms of a number of parameters pi (p1, p2, p3 and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, ways will be introduced in which parameters can be permitted to vary without being fully independent floating parameters. For the purposes of describing FIG. 5, only the variable parameters are considered as parameters pi.

504: A model target shape is estimated by setting initial values pi(0) for the floating parameters (i.e. p1(0), p2(0), p3(0) and so on). Each floating parameter will be generated within certain predetermined ranges, as defined in the recipe.

506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

508, 510: The measured diffraction pattern and the model diffraction pattern are then compared and their similarities and differences are used to calculate a "merit function" for the model target shape.

512: Assuming that the merit function indicates that the model needs to be improved before it represents accurately the actual target shape, new parameters p1(1), p2(1), p3(1), etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

514: When the merit function indicates that this iterative process has converged on a solution with a desired accuracy, the currently estimated parameters are reported as the measurement of the actual target structure.

The computation time of this iterative process is largely determined by the forward diffraction model used, i.e. the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 502 For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
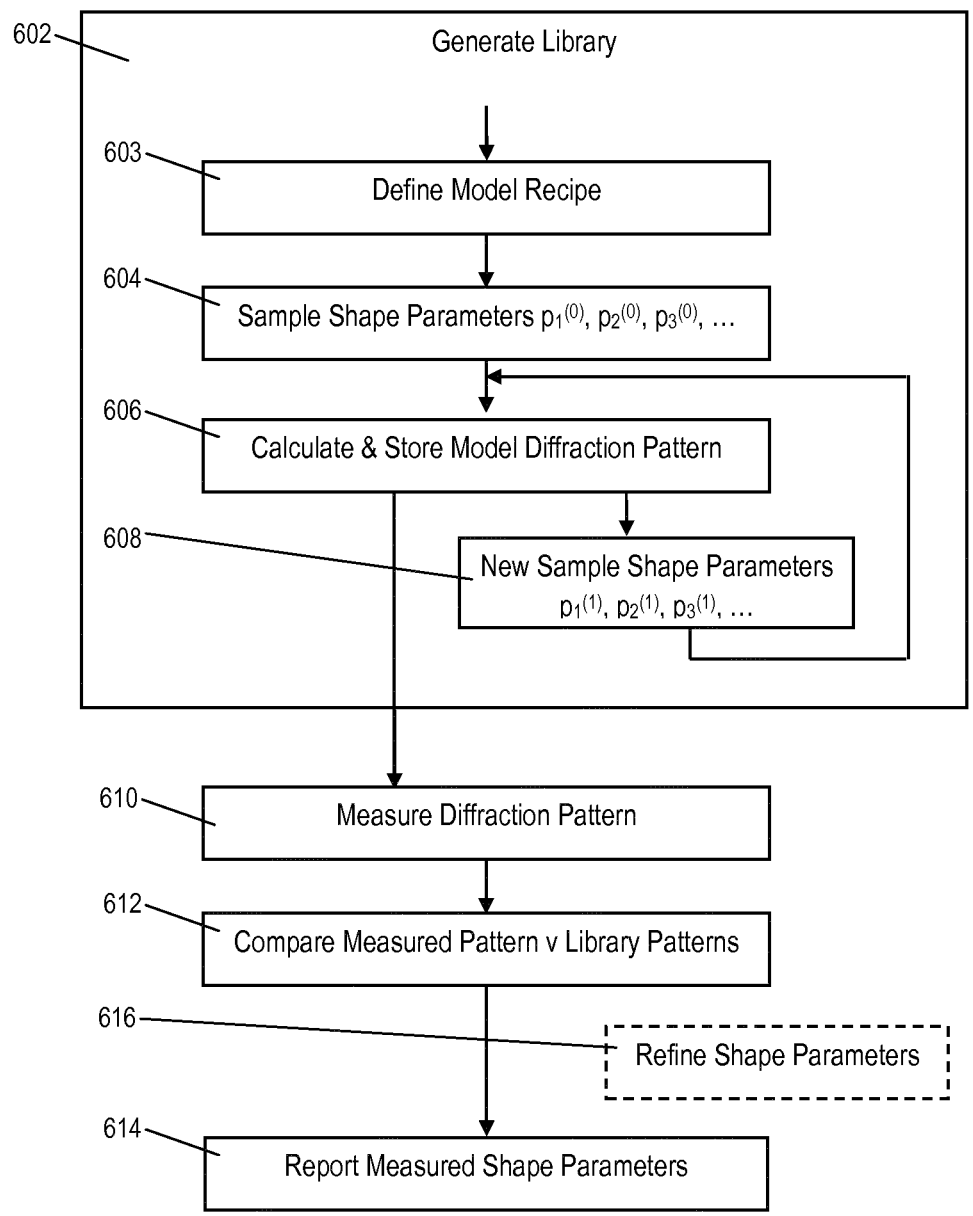
FIG. 6 depicts a second example process for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

602: The process of generating the library begins. A separate library may be generated for each type of target structure. The library may be generated by a user of the measurement apparatus according to need, or may be pre-generated by a supplier of the apparatus.

603: A 'model recipe' is established which defines a parameterized model of the target structure in terms of a number of parameters pi (p1, p2, p3 and so on). Considerations are similar to those in step 503 of the iterative process.

604: A first set of parameters p1(0), p2(0), p3(0), etc. is generated, for example by generating random values of all the parameters, each within its expected range of values.

606: A model diffraction pattern is calculated and stored in a library, representing the diffraction pattern expected from a target shape represented by the parameters.

608: A new set of shape parameters p1(1), p2(1), p3(1), etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

610: After the library is generated (though it could be before), the real target 30 is placed in the scatterometer and its diffraction pattern is measured.

612: The measured pattern is compared with the modeled patterns stored in the library to find the best matching pattern. The comparison may be made with every sample in the library, or a more systematic searching strategy may be employed, to reduce computational burden.

614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e. the calculation of the estimated model diffraction pattern using a rigorous optical diffraction theory from the estimated target shape.

Certain semiconductor structures comprise stacks of different layers. For example, 3D-NAND flash memory (also known as vertical NAND flash memory) is a memory architecture in which memory cells are stacked vertically into layer stacks. An individual memory cell may be made up of one planar polysilicon layer containing a hole filled by multiple concentric vertical cylinders. The hole's polysilicon surface acts as the gate electrode. The outermost oxide cylinder acts as the gate dielectric, enclosing a silicon nitride cylinder that stores charge, in turn enclosing an oxide cylinder as the tunnel dielectric that surrounds a central rod of conducting polysilicon which acts as the conducting channel.

The layer stacks may comprise a multilayer repeating structure of alternate layers of first material and a second material. Each layer pair is repeated more than 10 times. Each layer pair may be repeated more than 20 times or more than 30 times. In a specific example, each layer pair is repeated approximately 32 times. After these layers are grown, holes (channels) are etched through the layer stack with a very high aspect ratio, of the order of 1:50. To obtain good device performance, good control of the layer thicknesses and hole profile is important. This requires metrology of layer thickness and profile of the etched hole.

Metrology of the layers and the holes can be performed using cross-section scanning electron microscopy (SEM), but this is time consuming and destructive. Other techniques, such as optical critical dimension scatterometry and ellipsometry are not destructive but the measured data has insufficient information content to measure each individual layer in the stack.

Certain materials have absorption characteristics such that the level of absorption is dependent upon the wavelength of the absorbed radiation. One such material may be comprised within the layer stack. In one embodiment, the layer stack comprises a first material which has these absorption characteristics, alternating with a second material. For example, the first material may be polysilicon and the second material may be an oxide (for example, silicon dioxide). In the specific case of polysilicon, as the wavelength of radiation used for inspection is increased, the penetration depth of the radiation through the layer stack gradually increases and more layers can be seen. It should be appreciated that these techniques work most effectively on absorbing films.

As a consequence of this, metrology techniques may be used to measure physical properties of layers within the layer stack. Such techniques may comprise illuminating the layer stack with inspection radiation and detecting the resultant diffraction signal. By repeating these measurements with inspection radiation of different wavelengths, the physical properties of different layers can be measured. Consequently subsets of the layers comprised within the layer stack can be measured independently by performing measurements using inspection radiation of different wavelengths. In an embodiment, it is physical properties of layers comprising the second material which are being measured. Each subset may comprise a single layer, or more than one layers. Where they comprise more than one layer, each subset may comprise (for example) groups of adjacent layers of one material, e.g., the second material.

Figure 7:
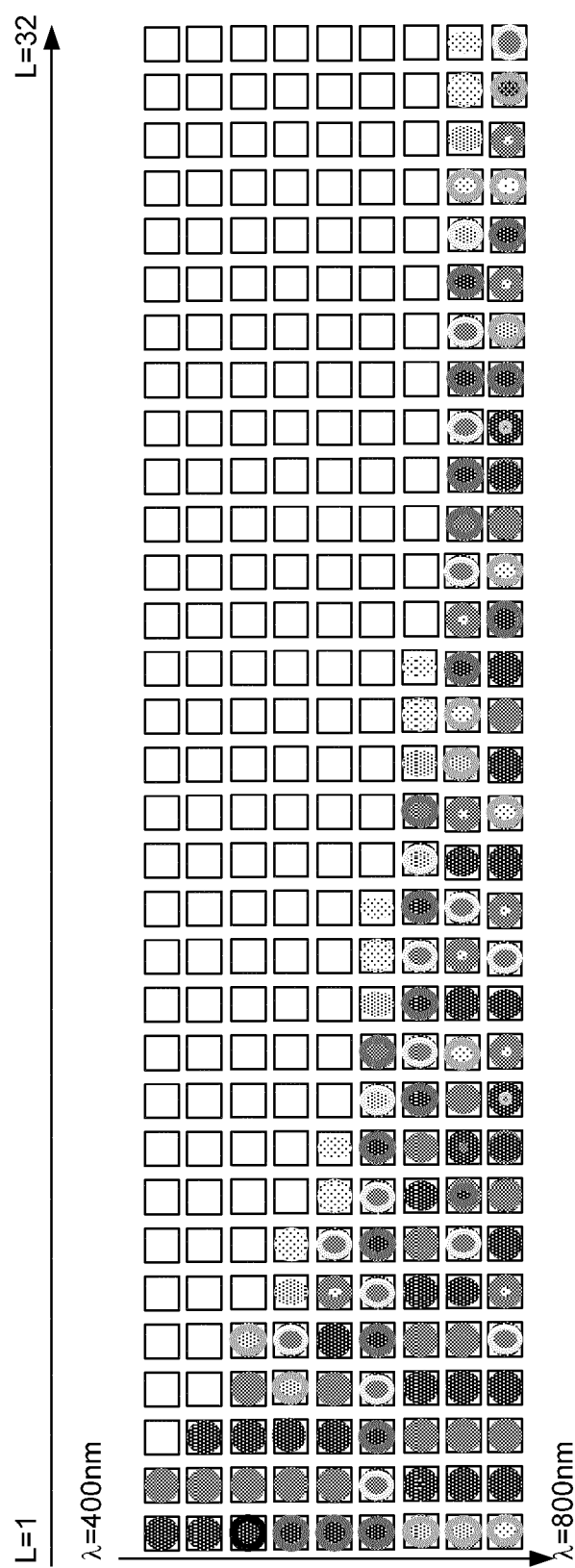
FIG. 7 schematically illustrates calculated sensitivity to structure properties at different layers of a structure for different wavelengths of inspection radiation.

FIG. 7 is a sensitivity plot showing the calculated sensitivity for thickness of the second material (in this example oxide) layer as a function of wavelength of the inspection radiation ($\lambda$-vertical direction) and layer index (L-horizontal direction). In the specific example illustrated there are 32 oxide layers (L=1-32) comprised in the layer stack, and the layer stack is inspected using inspection radiation of wavelength between 400 nm and 800 nm, in 50 nm intervals.

Where boxes are blank, there is no, or insufficient, calculated sensitivity for the corresponding oxide layer when inspected using inspection radiation of that wavelength, the inspection radiation having been absorbed in higher levels of the layer stack. Where boxes show a pupil pattern, the oxide layer is sensitive to the inspection radiation at that level, and reconstruction techniques may be used to model the oxide layer in a similar manner to those described in relation to FIGS. 5 and 6. In these reconstruction techniques, the floating parameters may be selected to be those describing the lowermost (sufficiently) sensitive layer(s), with parameter for other layers being fixed. Lowermost here is with respect to the (upper) illuminated surface.

For the shortest wavelength (in this example $\lambda$=400 nm) the diffraction signal is sensitive to physical properties of only the uppermost two layers of the layer stack. Consequently a reconstruction of the structure corresponding to the diffraction pattern resultant from using inspection radiation of this wavelength $\lambda$ may only have floating parameters describing these uppermost two layers. As the wavelength $\lambda$ gradually increases, more layers L start showing sensitivity. This property can be exploited by breaking the correlation (decorrelating) the layers. This can be done by "floating", i.e. describe in terms of floating parameters, only the (relevant physical properties of the) lowermost layers which show sufficient sensitivity to provide meaningful results, during reconstruction. Layers not floated are fixed, that is described in terms of fixed parameters. The layers described by fixed parameters may use the values calculated in previous reconstructions for which these layers were described by floating parameters (i.e., when they were the lowermost sensitive layers). Alternatively the fixed parameters may be estimated or calculated according to other methods or criteria.

As an example of the above, the first three steps of a basic reconstruction scheme may comprise:
  inspection of the structure using radiation at $\lambda$=400 nm:
    reconstruction of oxide layers 1 and 2;
  inspection of the structure using radiation at $\lambda$=450 nm:
    reconstruction of oxide layer 3 while keeping layers 1 and 2 fixed using results from the previous step ($\lambda$=400 nm);
  inspection of the structure using radiation at at $\lambda$=500 nm:
    reconstruction of oxide layers 4 and 5 while keeping layers 1, 2 and 3 fixed using results from the previous step ($\lambda$=450 nm).

These steps are repeated in a similar fashion for each wavelength, in each case reconstructing only one or more of the newly sensitive layers (i.e., the lowermost sensitive layers) while using the results from the previous reconstruction(s) for the already reconstructed layers, until all layers have been reconstructed (or another criterion is met). The order of the steps as presented above is for explanation only; in practice it is likely that all the inspection steps are performed first, followed by all of the reconstruction steps. Also light of multiple wavelengths may be used in the illumination step.

An initial sensitivity analysis may be performed so as to determine which layer(s) can be "floated" based on the wavelength of the illumination radiation used, and which layers should be kept "fixed" since they show insufficient sensitivity for illumination radiation of that wavelength.

This specific approach is provided purely by way of example, and should be sensitive to error propagation. However, more sophisticated algorithms can be used to improve robustness This basic idea can be extended such that the physical property being measures is the Dimension (CD) of the high-aspect ratio hole. This uses essentially the same approach as that described above for film thickness metrology, with the reconstruction parameters (both fixed and floating) describing the hole CD instead of layer thickness. The physical property may be a parameter other than layer thickness or hole CD.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc . . . The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g.

having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection method comprising:
  detecting a first diffraction signal arising from illumination of a structure using inspection radiation having a first wavelength, the structure comprising a plurality of layers; and
  determining a first property of a first subset of the plurality of layers from the first diffraction signal;
  detecting a second diffraction signal arising from illumination of the structure using inspection radiation having a second wavelength; and
  determining a second property of a second subset of the plurality of layers based on the second diffraction signal and the first property.

2. The method as claimed in claim 1, wherein:
  a third subset of the plurality of layers comprises a first material which absorbs some of the inspection radiation having the first wavelength; and
  a level of absorption, and a level of penetration of the inspection radiation having the first wavelength through the third subset of plurality of layers, is dependent upon the first wavelength.

3. The method as claimed in claim 2, wherein the first, second, and third subsets are arranged in alternate layers of the first material with layers of a second material, and the first and second subsets comprise the second material.

4. The method as claimed in claim 1, further comprising:
  illuminating the structure with the inspection radiation having the first wavelength; and
  illuminating the structure with the inspection radiation having the second wavelength.

5. The method as claimed in claim 1, wherein:
  the first and second wavelengths are selected from a plurality of wavelengths, and
  a range and/or a number of the plurality of wavelengths used is determined by material properties and a number of layers of the plurality of layers.

6. The method as claimed in claim 1, wherein:
  the first subset is positioned over the second subset, and
  the first diffraction signal is sensitive to the first property.

7. The method as claimed in claim 1, wherein:
  the determining the second property comprises performing a reconstruction of the second subset,
  during the reconstruction, the second property is described in terms of floating parameters, with the first property being described by fixed parameters.

8. The method as claimed in claim 7, wherein the first property is a result of reconstruction of the first subset.

9. The method as claimed in claim 7, further comprising:
  performing a sensitivity analysis on the plurality of layers to determine the first subset which its diffraction signal is sensitive to the first property.

10. The method as claimed in claim 7, wherein the second wavelength is longer than the first wavelength.

11. An inspection apparatus comprising:
  a detector configured to:
    detect a first diffraction signal arising from illumination of a structure using inspection radiation having a first wavelength, the structure comprising a plurality of layers; and
    detect a second diffraction signal arising from illumination of the structure using inspection radiation having a second wavelength; and
  a processor configured to:
    determine a first property of a first subset of the plurality of layers from the first diffraction signal; and
    determine a second property of a second subset of the plurality of layers based on the second diffraction signal and the first property.

12. The inspection apparatus as claimed in claim 11, further comprising:
  a radiation source configured to illuminate the structure with the inspection radiation having the first wavelength and the inspection radiation having the second wavelength.

13. The inspection apparatus as claimed in claim 11, wherein:
  the first and second wavelengths are selected from a plurality of wavelengths, and a range and/or a number of the plurality of wavelengths used is based on material properties of the structure and a number of layers of the plurality of layers.

14. The inspection apparatus as claimed in claim 11, wherein:
the first subset is positioned over the second subset, and
the first diffraction signal is sensitive to the first property.

15. The inspection apparatus as claimed in claim 11, wherein the processor is further configured to perform a reconstruction of the second subset, during the reconstruction, the second property is described in terms of floating parameters, with the first property being described by fixed parameters.

16. The inspection apparatus as claimed in claim 15, wherein the first property is a result of reconstruction of the first subset.

17. The inspection apparatus as claimed in claim 15, wherein the processor is further configured to perform a sensitivity analysis on the plurality of layers to determine the first subset, which its diffraction signal is sensitive to the first property.

18. The inspection apparatus as claimed in claim 15, wherein the second wavelength is longer than the first wavelength.

19. The inspection apparatus as claimed in claim 11, wherein the first, second, and third subsets are arranged in alternate layers of the first material with a second material, and the first and second subsets comprise the second material.

20. A lithographic apparatus configured to form a structure on a substrate, the structure comprising a plurality of layers, the lithographic apparatus comprising:
an inspection apparatus;
a detector configured to:
detect a first diffraction signal arising from illumination of the structure using inspection radiation having a first wavelength; and
detect a second diffraction signal arising from illumination of the structure using inspection radiation having a second wavelength; and
a processor configured to:
determine a first property of a first subset of the plurality of layers from the first diffraction signal; and
determine a second property of a second subset of the plurality of layers based on the second diffraction signal and the first property.

* * * * *